United States Patent [19]

Tanaka et al.

[11] Patent Number: 4,490,112
[45] Date of Patent: Dec. 25, 1984

[54] ORTHODONTIC SYSTEM AND METHOD

[75] Inventors: Susumu Tanaka, Suwa; Takehiko Daisaku, Kodaira; Yoshihide Suda, Tokyo, all of Japan

[73] Assignees: Kabushiki Kaisha Suwa Seikosha; Takehiko Disaku, both of Tokyo, Japan

[21] Appl. No.: 414,189

[22] Filed: Sep. 2, 1982

[51] Int. Cl.³ .............................................. A61C 7/00
[52] U.S. Cl. .................................................... 433/20
[58] Field of Search ........................... 433/20; 428/960

[56] References Cited

U.S. PATENT DOCUMENTS 4,037,324  6/1977  Andreasen ............................ 433/20

OTHER PUBLICATIONS

Effect of Low Temperature Phase Changes on Mechanical Properties of Alloys Near Composition T.N., by Buehler et al., Journal of Applied Physics vol. 34 No. 5, May 1961.

"Metals That Remember" by Hansen, Science 81, Jun. 81, pp. 44–47.

Primary Examiner—Robert Peshock
Attorney, Agent, or Firm—Blum, Kaplan, Friedman, Silberman & Beran

[57] ABSTRACT

An orthodontic system including an ultraelastic archwire having a transformation temperature of normal body temperature of about 37° C. is provided. Only a small load is applied to the teeth when the orthodontic system is disposed in a patient's mouth. An increased load is applied to the teeth only when the temperature in the mouth is increased by placing a material having a higher than body temperature in the mouth. As a result, the temperature in the patient's mouth can be controlled without inflicting pain during natural every day actions. The orthodontic effect is available intermittently by raising the mouth temperature for producing higher stress or load which serves to move the teeth orthodontically. The ultaelastic alloy is preferably Ni-Ti alloy containing at least about 50.5 atomic percent of nickel and preferably about 50.7 atomic percent.

11 Claims, 3 Drawing Figures

ORTHODONTIC SYSTEM AND METHOD

BACKGROUND OF THE INVENTION

This invention relates to a novel orthodontic system and orthodontic method for the orthodontic movement of malaligned teeth and more particularly to a system utilizing an ultraelastic material which applies a variable orthodontic load in response to temperature change.

Conventional systems for the orthodontic movement of teeth have usually been based on the elasticity of a metal wire. A load created by bending a metal wire is applied to the tooth to be corrected in order to move it in the direction of the load. Such conventional systems utilize orthodontic metal wires formed from stainless steel, a Co-Cr based alloy or an intensly worked Ni-Ti alloy. The elasticity of these wires is represented by the proportional elastic limit of the metal or alloy involved. The Ni-Ti alloy has a higher proportional elastic limit than the stainless steel or other alloys. However, the Ni-Ti alloy does not exhibit elongation exceeding about 2% in a tensile test. The stainless steel and other alloys show elongation which is less than 1%. Thus, if the wire is bent or pulled beyond its proportional elastic limits it undergoes plastic deformation. Excessive deformation is unpredictable in the conventional wires. This small proportional elastic limit means that the orthodontic effect obtained is relatively small.

The elasticity of the conventionally utilized metallic materials is an inherent property thereof which is difficult to modify by heat treatment or otherwise. Specifically, it is not possible to heat treat an intensively worked Ni-Ti alloy, since heat treatment reduces by about one-half the proportional elastic limits which has been obtained by the intense working. U.S. Pat. No. 4,037,324 utilizes one such alloy wherein a stoichiometric alloy of Ni and Ti, specifically the atomic ratio of Ni to Ti is 1:1. An orthodontic system based on this alloy presents practical problems when utilized in that a patient undergoes intense pain, often with the dental periosteum suffering from interruption in blood circulation. This occurs because the transformation temperature (which is the lowest temperature wherein the ultraelastic effect occurs) is 26.7° to 32.2° C., a temperature lower than normal body temperature. Thus, the large load is applied continually to the teeth at all times that the orthodontic system is disposed in the patient's mouth. This system based on the stoichiometric alloy of Ni and Ti is not fully satisfactory from the point of view of the patient's comfort.

Accordingly, it would be desirable to provide an orthodontic system which overcomes the shortcomings of the prior art systems. Such a system would apply a very small load to the teeth when the orthodontic system is disposed in a patient's mouth, and only apply an increase load when the temperature in the mouth is increased by taking in a material having a temperature above body temperature.

SUMMARY OF THE INVENTION

Generally speaking, in accordance with the invention, an orthodontic system including an orthodontic member which applies variable orthodontic load in response to a difference between normal body temperature and the temperature prevailing upon placement of a temperature affecting material in the mouth is provided. The orthodontic member is a Ni-Ti alloy containing about 50.5 to 51.0 atomic percent nickel with the balance titanium having a transformation temperature of about 37° C. or normal body temperature. This permits applying a very small load to the teeth when the orthodontic system is installed in a patient's mouth and increasing the orthodontic load to the teeth when the temperature in the mouth is increased by taking in a high temperature material, such as hot water. Utilizing a orthodontic system whose transformation temperature is about normal body temperature permits intermittently varying the orthodontic load applied to the teeth to promote orthodontic movement of the teeth more effectively. Preferably the orthodontic member in accordance with the invention is formed from a Ni-Ti alloy containing 50.7 atomic percent nickel.

Accordingly, it is an object of the invention to provide an improved orthodontic system.

It is another object of the invention to provide an improved orthodontic system for intermittently varying the load applied to promote orthodontic movement of teeth more effectively.

It is a further object of the invention to provide an improved orthodontic system wherein intermittently varying orthodontic loads are applied in response to the temperature of the patient's mouth.

Still a further object of the invention is to provide an improved orthodontic member for applying a varying orthodontic load in response to the temperature of the patient's mouth.

Yet another object of the invention is to provide an improved orthodontic system including an orthodontic member of a Ni-Ti alloy.

Yet a further object of the invention is to provide an improved orthodontic system wherein the orthodontic member is a Ni-Ti alloy containing from about 50.5 to 51.0 atomic percent nickel.

Another object of the invention is to provide an improved method of promoting orthodontic movement of teeth.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
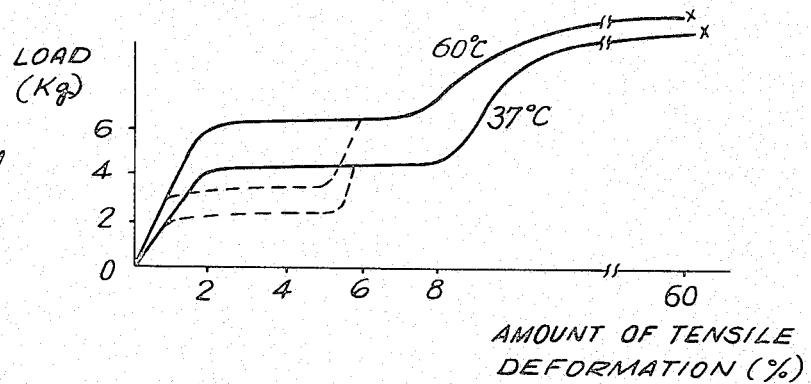
FIG. 1 are graphs illustrating the load-strain characteristics obtained from tensile test of an ultraelastic wire utilized in an orthodontic device prepared in accordance with the invention.

The physiological aspects of the orthodontic system constructed and arranged in accordance with the invention will now be described. Generally, a substantially constant orthodontic load has been applied in orthodontic systems. However, in accordance with the invention, an intermittently varying load is applied to promote orthodontic movement of the teeth effectively. More specifically, the orthodontic movement of the teeth in accordance with the invention utilizes a variation in the temperature in the mouth. The orthodontic member applies an orthodontic load which varies in response to a difference in the temperature of the mouth between normal body temperature (37° C.) and the higher or lower temperature wherein a high temperature effecting material, such as hot water or food, or a cold material, such as cold water or ice has been placed in the mouth. The orthondontic load increases in response to an increase in the temperature of the mouth. The orthodontic system in accordance with the invention facilitates effective orthodontic treatment, since the patient takes at least some of such temperature effecting materials every day. Additionally, such materials can be taken consciously so as to apply the orthodontic load selectively.

The application of an intermittently varying load to the human body is physiologically more effective, and can complete orthodontic treatment more quickly than application of a constant load. In accordance with the invention, it is sufficient normally to maintain a light orthodontic load. In fact, no load need be maintained when the mouth is at normal body temperature. A maximum load can be selected to be applied only when a certain temperature affecting material is placed in the mouth. Thus, it is possible to avoid pain or discomfort on the part of the patient to a great extent. A light load which is normally maintained is at a level which discomfort is negligible for the patient and will remove any mental discomfort during the time of orthodontic treatment which usually extends over an appreciable period of time.

Previously it was believed that maximum orthodontic force must be applied for moving the teeth. However, in accordance with the invention the orthodontic load is applied and released to move the teeth intermittently. A compressed region is formed on the dental periosteum on the side of the tooth in the direction in which it is being moved and formation of osteoclasts causes absorption on the alveolar wall. A pulled zone is formed on the dental periosteum on the opposing side. The activity of bone-forming cells results in addition on the opposite alveolar wall.

When the orthodontic system in accordance with the invention is utilized, the dental periosteum does not suffer from any interruption in blood circulation. This is due to the fact that maximum load bears only temporarily on the tooth and is maintained at a comfortable level otherwise. Additionally, the variable load promotes formation of the osteoclasts and bone-forming cells for enhancing the progress of the orthodontic treatment. Having discussed the advantages of the orthodontic system in accordance with the invention, a method for orthodontic treatment may be carried out by utilizing an orthodontic device which will not be described.

The orthodontic system in accordance with the invention is formed utilizing a material exhibiting ultraelasticity, for example an utlraelastic Ni-Ti alloy. Ultraelasticity is a property, entirely different from the proportional elastic limit of conventionally available metallic materials. An ultraelastic material returns to its original shape upon removal of the deforming load even if deformation of about 8% is imposed during a tensile test. This high elastic deformability permits bending or pulling required for any orthodontic purposes.

When the ambient temperature of the orthodontic device changes, the device applies a load which varies in response to the temperature change in such a fashion that the load increases with an increase in temperature. This is due to the fact that in the range of ultraelasticity, the stress (or load) is substantially constant, and is proportional to the temperature. The variation in stress (or load) with a change in temperature is a feature not found in other materials. This feature enables variation in orthodontic load with a temperature variation selectively caused by the temperature of a material placed in the mouth.

In order to provide an orthodontic device having these desired properties, it is not sufficient merely to utilize an ultraelastic Ni-Ti alloy, but it is necessary to select an appropriate alloy composition. Additionally, it is necessary to select appropriate conditions for the preparation of the orthodontic device by appropriate heat treatment. The utlimate properties of the orthodontic device can also vary with the shape of the device, for example the diameter of the wire or the cross-section. When these factors are appropriately considered with respect to one another, it is possible to provide the properties required for varying orthodontic purposes.

The orthodontic system in accordance with the invention will now be described in greater detail. Examples of ultraelastic metallic materials which can be utilized in accordance with the invention include various alloys. Such alloys may include intermetallic compounds of nickel and titanium, and also may be alloys of Cu and Zn; Cu, Zn and X, wherein X is Si, Sn, Al, etc.; Cu, Al and Ni; Au and Cd; Ag and Cd; Ni and Al; Cu, Au and Zn or Cu and Sn. The alloys are of the "thermoelastic" type having a superlattice and which undergo a martensitic transformation. Their ultraelasticity is derived from the martensitic transformation caused by stress at a temperature range above the martensitic transformation temperature and the inverse transformation thereof. There is only a small degree of hysteresis in the normal and reverse transformation between the austenite and the martensite; therefore, these alloys undergo crystallographically reversible transformation. Crystallographic reversibility means not only the restorability of the austenitic structure, but also of its original crystal orientation.

An ultraelastic alloy of nickel and titanium is polycrystalline. Thus, it is an optimum material for orthodontic devices, since it has excellent properties, including corrosion resistance. As a result of recent research, not only are Ni-Ti alloys available, but it possible to obtain alloys containing copper, iron or cobalt instead of the nickel and which have a controlled transformation temperature, a low degree of hysteresis and a small difference in ultraelasticity when a load is applied and when the load is removed.

The Ni-Ti alloy which contains at least 50.5 atomic percent nickel exhibits ultraelasticity of a temperature of about 37° C., which corresponds to the normal mouth or body temperature. An orthodontic member in accordance with the invention is formed preferably from an Ni-Ti alloy containing somewhat more nickel, namely about 50.7 atomic percent nickel was formed as follows.

A raw material containing 50.7 atomic percent nickel, with the balance being titanium, was melted at a high frequency vacuum furnace and the molten material was poured into a copper mold to form an ingot. The ingot was forged into a billet and the billet was diedrawn into a wire having a diameter of 0.4 mm. The wire rod was annealed during the drawing operation so that any further drawing thereof might be performed smoothly. The wire was polished to have a mirror surface and a final diameter of 0.37 mm. The wire was heat treated in a vacuum furnace to remove any strain created during the drawing operation and obtain ultraelasticity. The wire was heat treated under the following conditions:

Temperature: 700° C.;
Treating time: One hour;
Cooling: The wire was left in the furnace to cool slowly.

Figure 2:
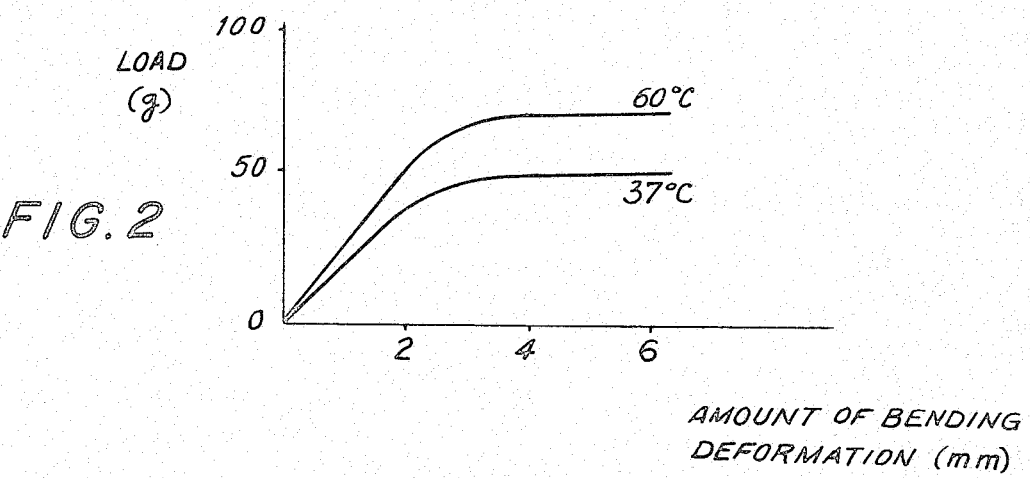
FIG. 2 are graphs showing the load-strain characteristics obtained from bending tests of the same wire utilized in FIG. 1.

The properties of the heat treated wire were as follows:

| | |
|---|---|
| Temperature at which martensitic transformation begins: | −40° C. |
| Temperature at which inverse martensitic transformation ends: | 5° C. |
| Load-strain characteristics found from a tensile test: | See FIG. 1 |
| Load-strain characteristics found from a bending test: | See FIG. 2. |

Referring now to FIG. 1, the load-strain characteristics of the wire are shown. The characteristics of the wire under load are shown by the solid line curves and the characteristics after removal of the load by the broken lines. Deformation and restoration of the wire took place at a fixed load both when the load was applied and removed. This is the feature called "ultraelasticity." The lower curve represents test results obtained at ordinary body temperatures of 37° C. The upper curve illustrates the results obtained at a temperature of 60° C. simulating the presence of a hot substance in the mouth. The graph indicates that a higher load for the same amount of deformation is obtained at the higher temperature, the same phenomenon occuring both under low and upon removal of the load.

FIG. 2 illustrates the bending characteristics of a 10 mm long wire secured at one end with the load applied to the other end. The curves indicate that a greater load occurs at 60° C. than at 37° C. for the same amount of deformation. This tendency corresponds to that obtained in the tensile tests. FIG. 2 also shows that the deformation of the wire beyond a certain level proceeds at a constant load. This feature is called "ultraelasticity in bending.".

The results of both the tensile and bending tests demonstrate that the orthodontic device in accordance with the invention undergoes deformation or restoration at a certain load depending upon the ambient temperature. This is true whether under load or after removal of the load. The load depends upon the martensitic transformation temperature of the material. More specifically, the ultraelastic load upon application thereof depends on the temperature at which the alloy begins martensitic transformation (Ms point), while the ultraelastic load upon removal thereof depends upon the temperature at which the alloy finishes inverse martensitic transformation (Af point).

In view of these characteristics it is necessary that the orthodontic device in accordacne with the invention be formed from a material capable of undergoing inverse martensitic transformation at a temperature below normal mouth temperature of 37° C. This is necessary in order to retain the ultraelasticity at a temperature of at least 37° C. It is, thus, necessary to employ an alloy containing between about 50.5 to 51.0 atomic percent, or preferably 50.7 atomic percent, of nickel the balance being titanium.

The transformation temperature of an alloy may be affected by its heat treatment conditions. It is, therefore, necessary to anticipate that the orthodontic device will be heat treated when it is installed, particularly by an orthodontist. Although it is desirable to employ a heat treating furnace wherein the temperature can be controlled, an orthodontist usually uses a more simple apparatus. The orthodontist will heat treat the wire by applying an electric current thereto and utilizing the heat generated by the electric resistance of the wire. A wire treated by this method cools quickly and tends to have a lower transformation temperature than that of a wire cooled slowly in a heat treating furnace.

In view of this, if a wire provided to an orthodontist can furnish inverse martensitic transformation at a temperature of 37° C. corresponding to normal body temperature, subsequent heat treatment lowers its transformation temperature to a level below 37° C. and insures the satisfactory elasticity of the device at normal body temperatures. Thus, it is possible to preset a somewhat higher transformation temperature to provide for any further reduction thereof brought about by the faster cooling rate upon installation.

An orthodontic device utilizing a wire formed in accordance with the invention will now be described by way of an example.

An ultraelastic wire is prepared in a straight form so that it may be utilized for a variety of purposes. It is, of course, possible to prepare a wire in the shape of an arch like an array of teeth. An easier method for obtaining a more precise shape to place an ultraelastic wire in a mold having a desired shape and heat treat the same. This method facilitates realization of very complicated shapes. An orthodontist may heat treat the wire at a temperature of 200° C. or higher.

Figure 3:
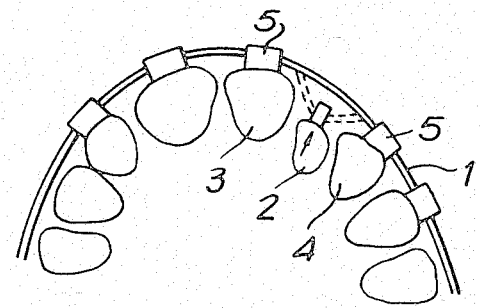
FIG. 3 is a schematic view illustrating the principle of the orthodontic movement of teeth utilizing the ultraelastic wire in accordance with the invention.

Referring now to FIG. 3, an ultraelastic archwire 1 is fastened to a tooth 2 to be moved, and a first normal tooth 3 and a second normal tooth 4 on both sides thereof. Wire 1 may be fastened to the teeth by following any conventional method in the art. For example, a bracket 5 can be bonded directly to each tooth, or welded to a metal ring fitted over a tooth. In FIG. 3, the pair of solid arcuate lines show the position of wire 1 fastened only to normal teeth 3 and 4, while the broken lines show the position of wire 1 fastened to the maladjusted tooth 2 also. Archwire 1 is placed under bending and tensile stresses along an array of teeth 3, 2 and 4 and a force (or load) which urges wire 1 to recover its original shape bears on tooth 2 in the direction of the arrow.

Tooth 2 is moved gradually by the load applied thereto and aligned correctly. Under normal circumstances, the temperature in the mouth is equal to the normal body temperature of 37° C., and therefore, ultraelastic wire 1 in accordance with the invention produces only a slight stress or load. However, once hot tea or coffee is taken into the mouth, or during a meal, the temperature of the wire is raised temporarily to a higher temperature in the range of, for example, 50° C. to 60° C. This elevated temperature produces a higher stress or load which serves to move tooth 2 orthdontically. If on the other hand, cold water, ice or any other substance having a lower temperature than the normal mouth temperature is taken in, wire 1 produces a smaller stress or load which at times may be zero. Intermittent application of the load as hereinabove described is quite effective orthodontically.

The orthodontic treatment of teeth with a device prepared in accordance with the invention is initiated if a hot or cold substance is placed in the mouth repeatedly. A correctly aligned array of teeth can be obtained usually after one to several months of such treatment. Although a simple example has been described, the invention is equally applicable to any more complicated orthodontic treatment of teeth. The use of an ultraelastic wire is even more effective for such complicated treatments. For example, the high elastic deformability of the ultraelastic wire in accordance with the invention enables more effective simultaneous correction of a plurality of malaligned teeth which have to be moved to different degrees.

It is obvious fom the foregoing description that the orthodontic system and orthodontic method in accordance with the invention provides a novel and effective means to correct the positioning of a malaligned tooth or teeth selectively during very natural every day actions, such as drinking hot or cold water and eating of meals, while relieving the patient of any orthodontic pain. The orthodontic device in accordance with the invention provides a host of advantages derived from full utilization of the ultraelasticity obtainable from an alloy prepared in accordance with the invention.

It will thus be seen that the objects set forth above, among those made apparent from the preceding description, are efficiently attained and since certain changes may be made in carrying out the above method and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly it is to be understood that in said claims, ingredints or compounds recited in the singular are intended to include compatible mixtures of such ingredients wherever the sense permits.

What is claimed is:

1. An orthodontic arch wire member comprising an alloy of the thermoelastic-type which undergoes a martensitic transformation caused by stress at a temperature above normal body temperature for selectively applying a variable orthodontic load in response to the difference between normal body temperature and a temperature in the mouth above normal body temperature caused by placing a temperature-affecting material having a temperature above normal body temperature in the mouth.

2. The orthodontic member of claim 1, wherein said alloy is formed of principally an intermetallic compound of nickel and titanium.

3. The orthodontic member of claim 2, wherein the inverse martensitic transformation of the Ni-Ti alloy terminates at a temperature below normal body temperature.

4. The orthodontic member of claim 3, wherein the Ni-Ti alloy comprises at least about 50.5 atomic percent nickel.

5. The orthodontic member of claim 5 having the shape of a wire with a diameter of about 0.4 mm before polishing 6. The orthodontic member of claim 3, wherein the Ni-Ti alloy comprises between about 50.5 and 51.0 atomic percent nickel with the balance titanium.

7. The orthodontic member of claim 3, wherein the Ni-Ti alloy comprises about 50.7 atomic percent nickel with the balance titanium.

8. The orthodontic member of claim 4, wherein a portion of the nickel is replaced by at least one of copper, iron and cobalt.

9. An orthodontic arch wire system comprising an orthodontic member comprising an orthodontic member comprising a thermoelastic-type alloy which undergoes a martensitic transformation caused by stress at a temperature above normal body temperature for selectively applying a variable orthodontic load to malaligned teeth in response to a temperature difference between normal body temperature and a temperature in the mouth above normal body temperature caused by placing a temperature-affecting material having a temperature above normal body temperature in the mouth.

10. An orthodontic method for the orthodontic arch wire movement of teeth comprising coupling to the teeth to be moved an orthodontic member which undergoes a martensitic transformation for select applying a variable orthodontic load in response to the difference between normal body temperature and a temperature caused by placing a temperature-affecting material in the mouth and selectively raising the temperature of the mouth to above normal body temperature to increase the orthodontic load applied to said teeth.

11. The orthodontic member of claim 1, wherein the inverse martensitic transformation of Ni-Ti alloy terminates at a temperature above normal body temperature.

* * * * *